US011642487B2

(12) United States Patent
Heimbuch et al.

(10) Patent No.: US 11,642,487 B2
(45) Date of Patent: *May 9, 2023

(54) REUSABLE RESPIRATORY PROTECTION DEVICE

(71) Applicant: Applied Research Associates, Inc., Albuquerque, NM (US)

(72) Inventors: Brian K. Heimbuch, Albuquerque, NM (US); Delbert A. Harnish, Albuquerque, NM (US); Geoffrey A. Kibble, Albuquerque, NM (US); Thomas B. Stephenson, Albuquerque, NM (US); Sheila J. Nogueira-Prewitt, Albuquerque, NM (US); Christopher G. Estkowski, Pullman, MI (US); Johnnie H. Copley, Minooka, IL (US); Graham Wilson, Flint (GB); Chris Ward, St. Asaph (GB)

(73) Assignee: Applied Research Associates, Inc., Albuquerque, NM (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/060,970

(22) Filed: Oct. 1, 2020

(65) Prior Publication Data
US 2021/0023326 A1   Jan. 28, 2021

Related U.S. Application Data

(63) Continuation of application No. 16/852,993, filed on Apr. 20, 2020, now Pat. No. 10,835,704.
(Continued)

(51) Int. Cl.
*A61M 16/10* (2006.01)
*A61M 16/06* (2006.01)
(Continued)

(52) U.S. Cl.
CPC ....... *A61M 16/1065* (2014.02); *A61L 2/0035* (2013.01); *A61L 2/206* (2013.01);
(Continued)

(58) Field of Classification Search
CPC .... A61M 16/06–0655; A61M 16/0605; A62B 18/025; A41D 13/1107
See application file for complete search history.

(56) References Cited

U.S. PATENT DOCUMENTS 3,161,491 A    12/1964   Gongoll et al.
5,647,356 A *   7/1997   Osendorf ............... A62B 27/00
                                             128/206.17
(Continued)

FOREIGN PATENT DOCUMENTS

CN         204637356 U    9/2015

OTHER PUBLICATIONS

European Patent Application No. 20806043.4, Extended Search Report dated May 24, 2022.

*Primary Examiner* — Joseph D. Boecker
*Assistant Examiner* — Thomas W Greig
(74) *Attorney, Agent, or Firm* — Erise IP, P.A.

(57) ABSTRACT

A reusable respirator including a mask adapted for covering and conforming to the face around the nose and a mouth of a user, a strap configured to secure the mask to a face of the user, and a filter component. All components of the respirator are capable of being cleaned, disinfected and sterilized at temperatures in excess of 50° C. An outer surface of the mask is substantially smooth and wettable for easily disinfecting and is shaped with a pair of outer shield portions for housing particulate air filters. The outer shield portions each include a closeable vent through the outer surface that is adapted to provide a user seal check and direct air flow through the outer surface for filtering by the respective particulate air filter, which is adapted to filter at least 95% of airborne particles.

20 Claims, 11 Drawing Sheets

Related U.S. Application Data

(60) Provisional application No. 62/848,341, filed on May 15, 2019.

(51) Int. Cl.
*A61L 2/20* (2006.01)
*A61L 2/00* (2006.01)

(52) U.S. Cl.
CPC .... *A61M 16/0605* (2014.02); *A61M 16/0683* (2013.01); *A61L 2202/22* (2013.01); *A61M 2202/203* (2013.01); *A61M 2202/206* (2013.01); *A61M 2209/088* (2013.01)

(56) References Cited

U.S. PATENT DOCUMENTS

| | | | | |
|---|---|---|---|---|
| 8,342,179 B2* | 1/2013 | Hacke | A61M 16/06 128/206.17 |
| 2004/0025880 A1* | 2/2004 | Capon | A62B 23/02 128/206.17 |
| 2004/0226563 A1* | 11/2004 | Xu | A62B 18/02 128/206.23 |
| 2012/0103339 A1* | 5/2012 | Koehler | A62B 18/02 128/206.14 |
| 2014/0261437 A1* | 9/2014 | Catanzarite | A62B 19/00 128/206.17 |

* cited by examiner

REUSABLE RESPIRATORY PROTECTION DEVICE

RELATED APPLICATIONS

This patent application is a continuation application claiming priority benefit, with regard to all common subject matter of U.S. patent application Ser. No. 16/852,993, filed Apr. 20, 2020, and entitled "REUSABLE RESPIRATORY PROTECTION DEVICE" ("the '993 application"). The '993 application claims priority benefit of U.S. Provisional Patent Application No. 62/848,341, filed, May 15, 2019, entitled "Reusable Respiratory Protection Device." The identified earlier-filed patent applications are hereby incorporated by reference in their entirety into the present application.

STATEMENT OF FEDERALLY SPONSORED RESEARCH OR DEVELOPMENT

This invention was made with government support under Contract No. HHSO100201700032C awarded by the Department of Health and Human Services, Office of the Assistant Secretary for Preparedness and Response, BiomedicalAdvanced Research and Development Authority. The government has certain rights in the invention.

BACKGROUND

1. Field

Embodiments of this disclosure relate generally to face masks for respiratory protection. More specifically, embodiments of this disclosure relate to an elastomeric half-mask respirator that prevents at least 95% of most airborne particles (most penetrating particle size is approximately 0.3 µm) from penetrating the mask (e.g., "N95" filter class).

2. Related Art

Various disposable N95 filter masks intended for single use are known. Additionally, many elastomeric half-masks that are reusable have been described, but these generally have one or more drawbacks that limit their appropriate reuse in a health care setting. For example, most existing masks generally require replaceable filter cartridges, include exhalation valves, may not be capable of being cleaned at high temperatures (e.g., greater than 50° C.), are not autoclavable, contain filtration media that cannot be cleaned and/or disinfected, and/or are not designed to limit bioburden accumulation.

SUMMARY

Embodiments of this disclosure provide an elastomeric half-mask respirator that is reusable and adapted to filter at least 95% of airborne particles for both non-oil-based and oil-based aerosols as well as viable and non-viable microorganisms (e.g., N95, R95, P95, N99, R99, P99, N100, R100, P100 filter class), thereby limiting penetration of airborne particles through the mask to less than 5% of the most penetrating size (e.g., 0.3 µm). Embodiments disclosed herein are cleanable at temperatures exceeding 50° C., autoclavable, designed with surfaces that can be easily cleaned, and may be embodied in a single piece that includes integrated head straps and filters that do not require removal during cleaning, disinfection, or sterilization. In certain embodiments, the head straps and filters are detachable and capable of being reprocessed as separate components and/or being replaced. Reprocessing protocols (cleaning, disinfection, and/or sterilization) enable reusability of the respirator. In certain embodiments, a quick field reprocessing protocol enables additional reuses between extended reprocessing protocols, which are further described below as including more thorough reprocessing treatments (e.g., washer-disinfector, autoclave, etc.).

In an embodiment, a reusable respiratory protection device includes a mask adapted for covering a portion of a user's face. The mask includes a face seal adapted to conform to a user's face around a nose and a mouth of the user, an outer surface, at least one outer shield portion formed in the outer surface, and at least one closeable vent through the at least one outer shield portion. The reusable respiratory protection device further includes at least one particulate air filter adapted to filter at least 95% of airborne particles. The at least one particulate air filter is housed within the at least one outer shield portion. The at least one closeable vent is adapted to direct air flow through the outer surface for filtering by the at least one particulate air filter. The outer surface is substantially smooth to mitigate bioburden accumulation and wettable to allow for cleaning, disinfection, or sterilization thereof. A strap is configured to secure the mask to the user's face.

In another embodiment, a reusable respirator includes a unitary mask formed of a single piece of material adapted for covering a portion of a user's face. The mask includes a face seal adapted to conform to a user's face around a nose and a mouth of the user, an outer surface, a first outer shield portion formed in the outer surface, a first vent through the first outer shield portion, a second outer shield portion formed in the outer surface, and a second vent through the second outer shield portion. A first particulate air filter, housed within the first outer shield portion, is adapted to filter at least 95% of airborne particles. A second particulate air filter, housed within the second outer shield portion, is adapted to filter at least 95% of airborne particles. The first vent and the second vent are each adapted to direct air flow to the first particulate air filter and the second particulate air filter, respectively. The outer surface of the mask is substantially smooth to mitigate bioburden accumulation and wettable to allow for cleaning, disinfection, or sterilization thereof.

In yet another embodiment, a method for processing a respirator for reuse includes a) providing a reusable respirator. The reusable respirator includes a mask adapted for covering a portion of a user's face. The mask includes a face seal adapted to conform to a user's face around a nose and a mouth of the user, an outer surface, at least one outer shield portion formed in the outer surface, and at least one closeable vent through the at least one outer shield portion. At least one particulate air filter, housed within the at least one outer shield portion, is adapted to filter at least 95% of airborne particles. The at least one closeable vent is adapted to direct air flow through the outer surface for filtering by the at least one particulate air filter. The outer surface is substantially smooth and wettable to allow for disinfection thereof. A strap is configured to secure the mask to the user's face. The method further includes b) using the reusable respirator in a field, and c) performing an extended reprocessing protocol.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages will be apparent from the following detailed description of the embodiments and the accompanying drawing figures.

BRIEF DESCRIPTION OF THE DRAWING FIGURES

Embodiments of this disclosure are described in detail below with reference to the attached drawing figures, wherein.

Figure 1:
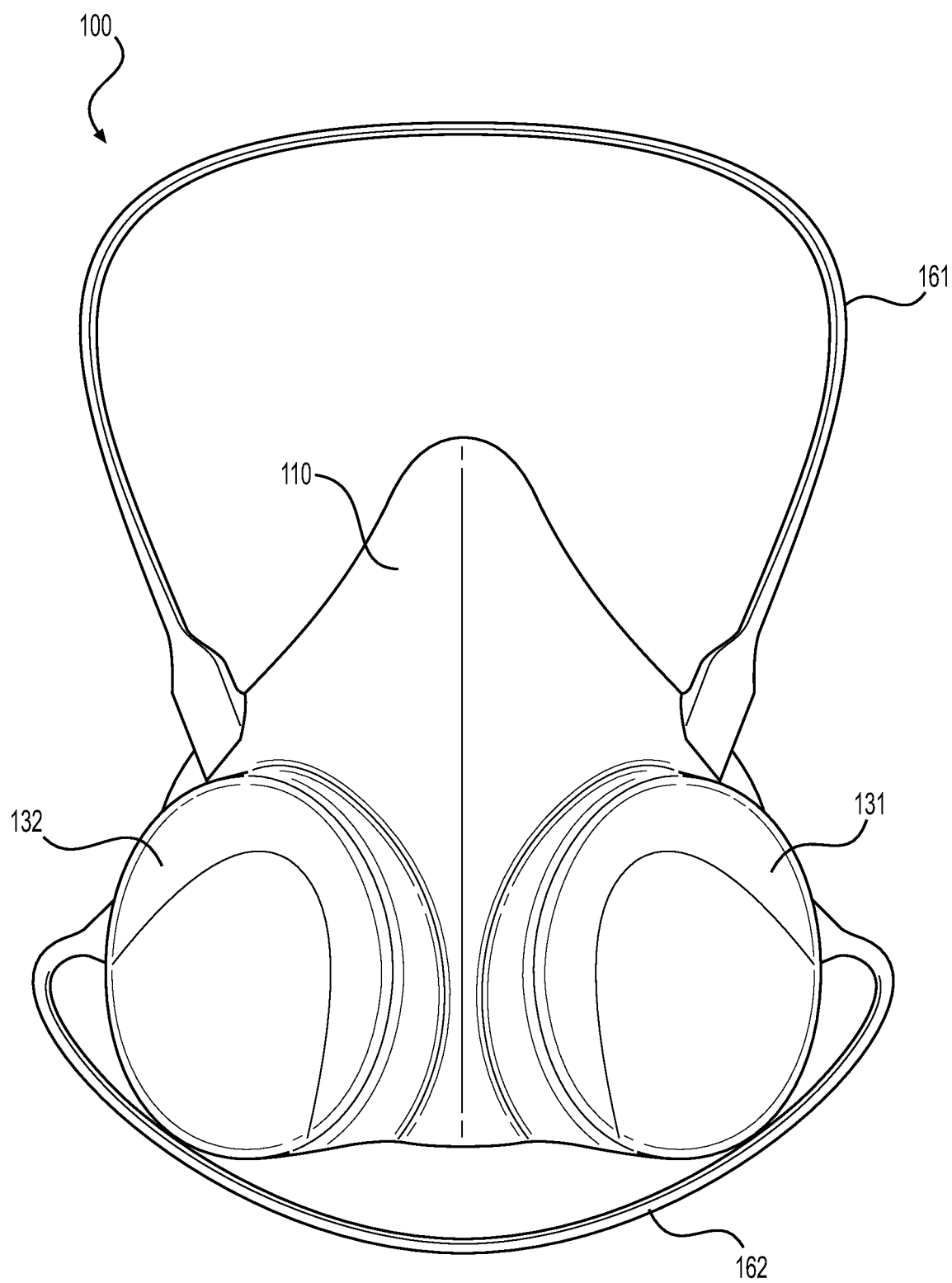
FIG. 1 is a first embodiment of a reusable respiratory protection device.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," "the embodiment," or "embodiments" mean that the feature or features being referred to are included in at least one embodiment of the technology. Separate references to "one embodiment," "an embodiment," "the embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the technology can include a variety of combinations and/or integrations of the embodiments described herein.

Respirators provide respiratory protection against atmospheres with airborne respiratory hazards (e.g., particles, microorganisms, dusts, mists, oils) including viable and non-viable airborne particles. Air-purifying respirators are designed for use in an atmosphere that provides adequate oxygen to support life since no supplemental oxygen is provided (as in a self-contained breathing apparatus). Respirators can be powered or unpowered. Powered air-purifying respirators (PAPRs) supply filtered air to a mask with a positive pressure air blower that may or may not be breath-assisted. Non-powered air-purifying respirators use the user's negative inhalation pressure to draw ambient air through filters to remove particulates from the ambient air and use a positive pressure exhaled from the wearer to trap any particulates that may be exhaled.

Non-powered air-purifying respirators generally fall into one of two categories: 1) filtering facepiece respirators (FFRs), or 2) half-mask elastomeric respirators (HMERs). FFRs are generally respirators in which the facepiece is formed of the filter material in either a preformed "cup" style, flat fold type, or duck bill type. FFRs are generally designed for single use because the filter material is not wettable per manufacturer guidance, which prevents the FFR from being cleaned, disinfected or sterilized (e.g., washed or disinfected with a disinfectant solution, washer-disinfector, ultrasonicator, sterilized via steam autoclave, chemical sterilant, etc.) for subsequent reuse. FFRs are also constructed using materials and methods that are not intended to support reusability (e.g., durability). FFRs are lighter than half-mask elastomeric respirators and typically discarded after a single use to avoid acting as a fomite by spreading infectious diseases, making them preferred in health care settings. Many FFRs are approved by the National Institute for Occupational Safety and Health (NIOSH) and cleared for use in hospital settings by the U.S. Food & Drug Administration (FDA). During an infectious disease pandemic, such as an influenza or coronavirus pandemic, a large number of respirators are needed, especially for health care workers. Single-use respirators, such as FFRs, will quickly be consumed during a pandemic lasting weeks or months, thus requiring an alternative approach to stockpiling and meeting the expected demand.

HMERs generally include a molded facepiece to which replaceable filtering cartridges may be attached. The mask itself is reusable, whereas the filtering cartridges are generally replaceable since the filter material cannot be cleaned or decontaminated (e.g., washed, disinfected, or steam sterilized) because they cannot be wetted per manufacturer guidance. Cleaning of HMERs in hospitals is time consuming, tedious, and prone to error for use, and they are not designed to withstand the moisture, temperature, and pressures of autoclaves and washer-disinfectors. HMERs also contain a number of grooves, crevices, materials, and design features that render them difficult to clean. Additionally, HMERs have not been cleared for use in the medical setting by the U.S. FDA.

Embodiments of this disclosure provide a single-piece HMER that is reusable and adapted to filter at least 95% of the most penetrating airborne particles. Respirators providing at least 95% efficiency at filtering airborne particles of the most penetrating size are referred to as being in the "P-, R-, or N95" filter class, per 42 C.F.R. Part 84. In other embodiments, the filter may be adapted to achieve higher levels of filtration efficiency in accordance with NIOSH requirements for P-, R-, or N99 filters and/or P-, R-, or N100 filters. N-series filters are restricted for use in environments free of oil aerosols. The R- and P-series filters are intended for removal of any particulate that includes oil-based liquid particulates. In addition to filtration efficiency, embodiments of the filter will meet or exceed (e.g., lower than maximum value) the maximum inhalation resistance and exhalation resistance values as defined in 42 CFR Part 84. Embodiments disclosed herein differ from conventional HMERs in that the filter media can be disinfected and/or sterilized via aqueous cleaning mechanisms (detergents, alcohol, bleach, etc.) and sterilization practices to effectively remove and/or otherwise render inert all contamination species. Certain embodiments include integrated or detachable straps, allowing the device to be donned similar to current FFRs. Certain embodiments include fixed or removable filters, allowing for integrated or separate reprocessing, respectively. The result is a sustainably reusable fully integrated respirator meeting NIOSH requirements as defined in 42 CFR Part 84 for a P-, R-series, or N-series filter with at least 95% filtration efficiency (e.g., P95, P99, P100, R95, R99, R100, N95, N99, N100). Additionally, the respirator provides an assigned protection factor greater than or equal to 10 as required for air-purifying respirators by the Occupational Safety and Health Administration under 29 CFR 1910.

FIG. 1 is a frontside view of an exemplary reusable respiratory protection device 100, which includes a mask 110 and straps 161, 162 configured for wearing on a user's face. The reusable respiratory protection device 100 may be referred to herein as "respirator 100" for short. The respirator 100 is an example of an elastomeric half-mask reusable respirator. Specifically, in one embodiment, the mask 110 is a half mask, meaning that it covers the lower half of the user's face including the nose and mouth, but not the eyes. The respirator 100 is adapted to be lightweight for improved comfort, especially for health care workers who may wear a respirator for long durations. For example, the respirator 100 is adapted to be lighter than existing elastomeric half-mask respirators due to the use of lighter and fewer materials. In certain embodiments, the mask weighs between about 3-oz. to about 4-oz. In other embodiments, the mask may weigh between 2-oz.-5 oz, or less than 2-oz, or greater than 5-oz.

The respirator 100 is adapted to have a shelf life longer than that of existing N95 FFRs, which is typically three to five years, due to the use of more durable materials and construction. In certain embodiments, the rated shelf life of respirator 100 is expected to be between ten and twenty years.

The mask 110 and straps 161, 162 provide a substantially smooth semi-rigid protective surface adapted for compatibility with cleaning and disinfection wiping protocols, which extends the life cycle of respirator 100 by allowing it to sustain numerous disinfections and/or sterilization cycles. Specifically, the mask 110 and straps 161, 162 include a smooth wettable surface that is adapted to be easily cleanable. The mask 110 and straps 161, 162 lack small edges, corners, and nooks to make surfaces easily accessible for wiping with disinfectant to avoid bioburden, such as a buildup of microorganisms. The mask 110 and straps 161, 162 are made of a material that is resistant to common disinfectants, such as isopropyl alcohol, benzalkonium chloride, hypochlorite or quaternary amines, for example. An exemplary material for the mask 110 and/or straps 161, 162 is silicone.

In one embodiment, due to the fact that the mask 110 and straps 161, 162 can be molded as a single piece of material, this feature further enables rapid and effective cleaning since the mask 110 and straps 161, 162 lack creases, bond lines, or other mechanical connections between separate components that could accumulate bioburden. Specifically, the mask 110 can be a unitary piece that includes a face seal 150 (described below in connection with FIG. 4), a first outer shield portion 131 and a second outer shield portion 132 formed in an outer surface of the mask 110 (described below in connection with FIG. 2) and a first vent 171 and a second vent 172 through the first and second outer shields 131, 132, respectively (described below in connection with FIG. 4). The single piece design also enhances the ability of the respirator 100 to withstand an automated cleaning regimen for rapid and repeated cleaning/sterilization without degradation that otherwise might initiate along bond lines or other mechanical connections.

Figure 2:
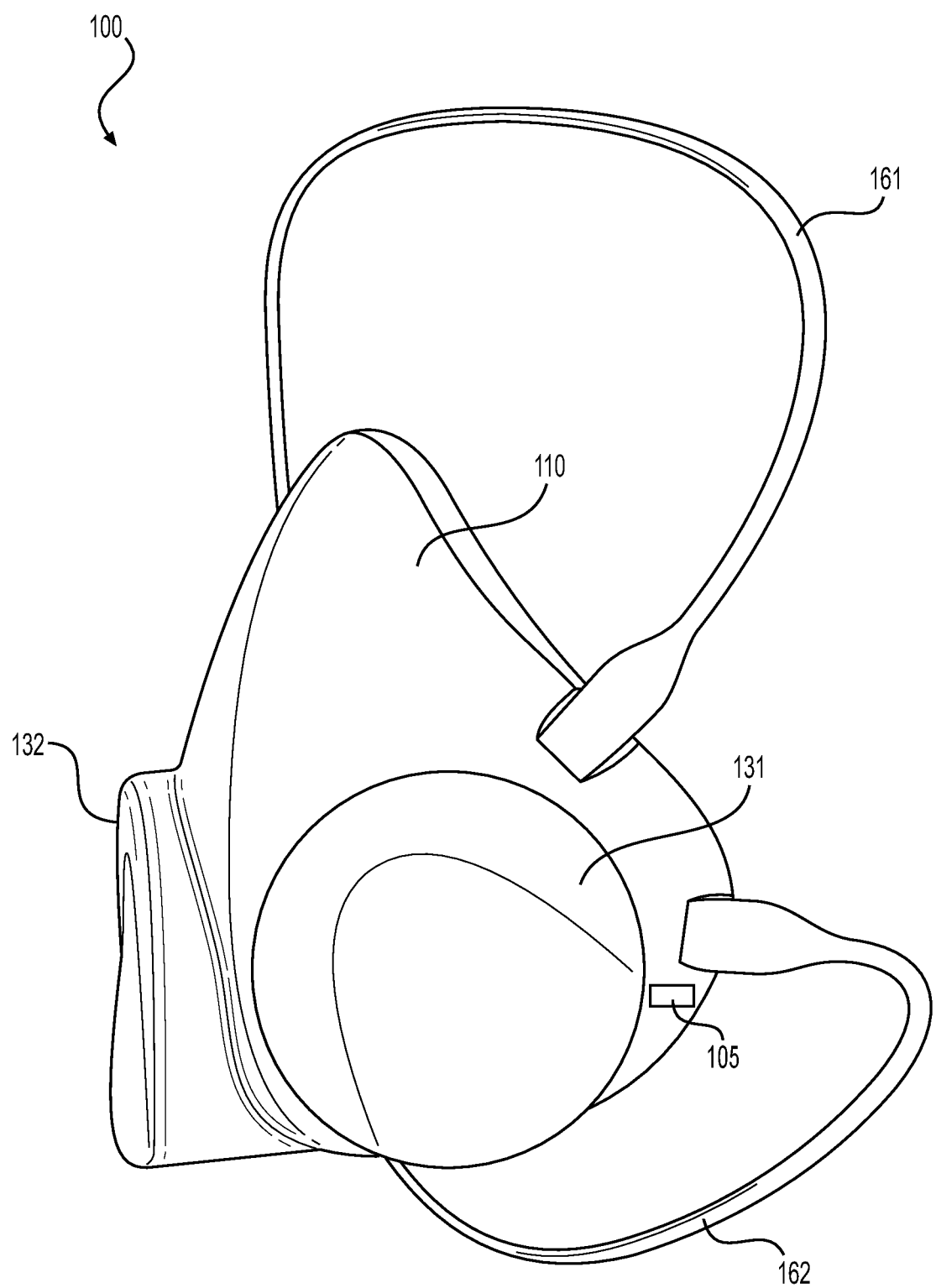
FIG. 2 is a perspective view of the reusable respiratory protection device of FIG. 1.

FIG. 2 is a perspective view of respirator 100 of FIG. 1. FIGS. 1 and 2 are best viewed together with the following description. The first outer shield portion 131 and the second outer shield portion 132 are portions of the mask 110 that protrude from the front of the mask 110 on either side (e.g., left or right). The first and second outer shield portions 131, 132 are formed as part of the material of the mask 110 and shaped to house and protect an inner filter material for purifying air (e.g., particulate air filters 141, 142, described below in connection with FIGS. 3 and 5). Specifically, the outer shield portions 131, 132 each forms a protective pocket for housing and protecting the inner filter material (e.g., protective pockets 133, 134 described below in connection with FIG. 6). The outer shield portions 131, 132 serve as a splashguard to protect the inner filter material from fluids that may be burdened with biological contamination (e.g., blood, saliva, and cough/sneeze droplets). The outer shield portions 131, 132 also provide protection of the inner filter material from damage due to impact.

Figure 3:
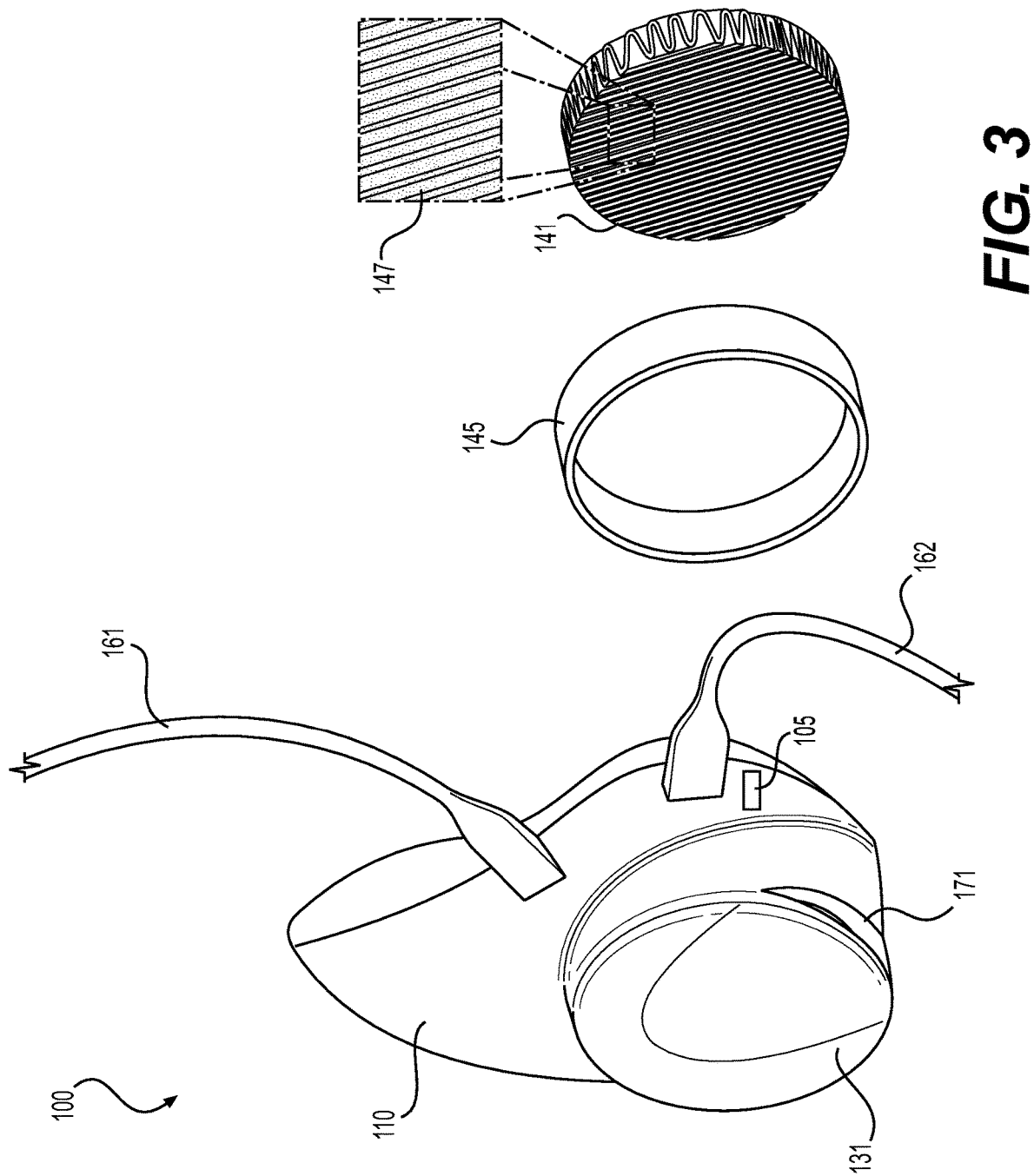
FIG. 3 is an exploded view of the reusable respiratory protection device of FIG. 1.

Straps 161, 162 provide an integrated harness for maintaining the mask 110 comfortably against the user's face. The strap may be formed of a single piece of material or two or more pieces of material. For example, as depicted in FIGS. 1-3, the strap includes an upper strap 161 and a lower strap 162, but alternative strap arrangements may be employed without departing from the scope hereof. For example, a unitary strap having an upper band and a lower band may be employed. An exemplary material for the strap is silicone, however other elastomeric, stretchable, and/or conformable materials may be used. This enables the strap to be stretched for assisting with donning and doffing the respirator 100, such that the strap has a first elongated length when stretched for placing over the user's head, and a second contracted length while being worn to securely maintain the mask 110 on the user's head. In some embodiments, the fixed contracted length of the strap may be adapted for a specified size range (e.g., to provide proper fit for different head sizes). However, the strap may optionally include a length-adjusting feature (e.g., a gathering clip), without departing from the scope hereof. The strap may be attached to the mask 110 in an integrated or detachable manner. To prevent hearing impairment, the strap is adapted to avoid the user's ears. As further described below, the strap is adapted to be easily cleaned and sterilized together with the mask 110 without needing to be detached. In other embodiments, the straps can be detached for cleaning, disinfection and/or sterilization.

Figure 5:
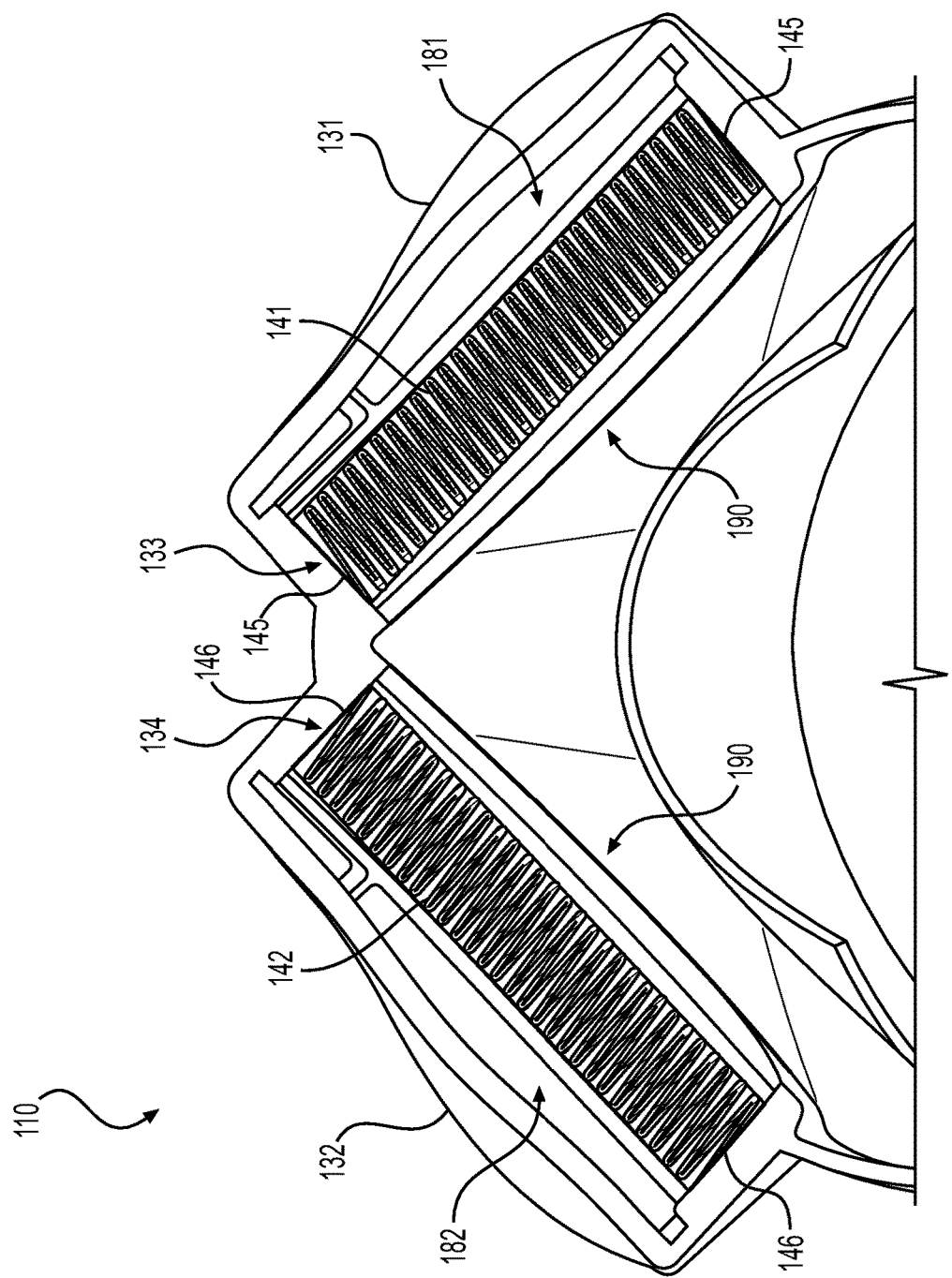
FIG. 5 is a cross-sectional bottom view of the mask of the reusable respiratory protection device of FIG. 1, in an embodiment.

FIG. 3 is an exploded view of respirator 100 for viewing internal components. Not all components of respirator 100 are depicted in FIG. 3 for clarity of illustration. The respirator 100 includes the mask 110, the straps 161, 162, a first particulate air filter 141, and a first filter rim 145 adapted for holding the first particulate air filter 141. A second particulate air filter 142 and a second filter rim 146 are shown in FIG. 5. In certain embodiments, each particulate air filter 141, 142 is surrounded about its circumferential edge by a respective filter rim 145, 146. In some embodiments, the filter rim 145, 146 may be made of polypropylene, although other materials (e.g., silicone) may be used. In some embodiments, the particulate air filters 141, 142 and the filter rims 145, 146 may be formed together by overmolding. Each particulate air filter 141, 142, secured within its respective filter rim 145, 146, can then inserted be into one of the outer shield portions 131, 132 of the mask 110. The mask 110 is configured such that the outer shield portions 131, 132 stretch to form a tight seal around each of the air filters 141, 142, respectively. In certain embodiments, the air filters 141, 142 may be sealed to the mask 110 via overmolding or other appropriate manufacturing process. Each of the air filters 141, 142, and its respective filter rim 145, 146, may be inserted into one of the outer shield portions 131, 132 of the mask 110 by hand, or by automated methods (e.g., robotics), or other manufacturing methods (e.g., overmolding). In some embodiments, the air filters 141, 142 are removable from the mask 110, but in other embodiments the air filters 141, 142 are not removable.

In some embodiments, the first vent 171 provides an air passage that connects the first particulate air filter 141 to outside the mask 110. Similarly, the second vent 172 (see FIG. 4) provides an air passage that connects the second particulate air filter 142 to outside the mask 110. In one embodiment, the first and second vents 171, 172 face downwardly and back towards the user and are further described below in connection with FIGS. 4-6.

In one embodiment, the first and second particulate air filters 141, 142 are made of a filter media or other material adapted to purify respirable air by filtering airborne particles, which prevents inhalation of the particles by the user of respirator 100. The filter media may be pleated, with a number of pleats being adapted for improved ventilation. Pleating the media increases the filter surface area which reduces breathing resistance. Other embodiments may use non-pleated media.

In an embodiment, first and second particulate air filters 141, 142 are adapted to exceed NIOSH requirements for the P-, R-, or N95 filter class. Other embodiments contain air filters adapted to exceed NIOSH requirements for the P-, R-, or N99 filter class, or P-, R-, or N100 filter class. In some embodiments, the particulate air filters 141, 142 are adapted to meet or exceed the European EN 143 guidance requirements. The thickness of the particulate air filters 141, 142 is adapted to be thin enough to maximize the amount of pleated or non-pleated media in the respirator to improve ventilation, lower breathing resistance, and increase speech intelligibility. A pressure drop across the particulate air filters 141, 142 may be used to measure the relative ease of breathing while wearing a respirator. For example, the NIOSH-mandated maximum inhalational pressure drop for an N95 respirator is 25 mm-$H_2O$. The respirator 100 is adapted to meet or exceed (lower than max value) this maximum inhalation pressure drop even after numerous cleaning/sterilizing protocols (e.g., see the extended reprocessing protocol Step 210, described below in connection with FIG. 7). A target goal of 10 mm-$H_2O$ has been established by Project BREATHE (Radonovich L. et al., Better respiratory equipment using advanced technologies for healthcare employees (Project B.R.E.A.T.H.E.): A report of an interagency working group of the U.S. federal government. 2009. http://www.publichealth.va.gov/docs/cohic/projectbreathe-report-2009.pdf). In certain embodiments, the respirator 100 may be adapted to meet or exceed this goal pressure drop.

Each of the first and second particulate air filters 141, 142 may include a protective coating or protective layer 147 disposed on one or both sides of the filter media, in some embodiments. The protective coating/layer 147 is substantially air permeable and substantially hydrophobic to mitigate contamination and wetting of the filter media for prolonging its integrity. The protective coating/layer 147 is, for example, a polypropylene or polyethylene layer that would protect the inner layer. In some embodiments, the filter media contains a polytetrafluoroethylene (PTFE) layer, which is substantially air permeable and substantially hydrophobic. The PTFE layer is preferably located between two protective layers 147 or affixed to a single protective layer 147. The particulate air filters 141, 142 may include other types of filter media, without departing from the scope hereof, such as high-efficiency particulate air (HEPA) filters and ultra-low particulate air (ULPA) filters or vapor capture materials (e.g., carbon). Other types of filter media such as microglass may be used without departing from the scope hereof, although a non-shedding filter media is preferable for durability and user safety.

In some embodiments, the first and second particulate air filters 141, 142 are capable of being cleaned, disinfected, and/or sterilized. In some embodiments, the particulate air filters 141, 142 may be cleaned with detergents and/or enzymes using manual or automated methods. In some embodiments, the particulate air filters 141, 142 may be cleaned using ultrasonic baths and/or washer-disinfectors. In other embodiments, particulate air filters 141, 142 may be disinfected with isopropyl alcohol, bleach, hydrogen peroxide, or other known disinfectants. In other embodiments, particulate air filters 141, 142 may be sterilized using an autoclave, gamma radiation, VHP, EtO, or other known sterilization methods. In some embodiments, the particulate air filters 141, 142 may be cleaned, disinfected, and/or sterilized while still housed within the respirator 100. In other embodiments, particulate air filters 141, 142 may be removed from the respirator 100 for separate cleaning, disinfecting, or sterilization.

The mask 110 may include an optional inner layer 190, in some embodiments, located between the first and/or second particulate air filter 141, 142 and the user for reducing accumulation of breath secretions on the first and second particulate air filters 141, 142. The inner layer 190 may include a removable washable, flexible insert (e.g., scrim) that provides a protective surface covering each of particulate air filters 141, 142 on the innermost portion of the mask 110 facing the user. In other embodiments, the inner layer 190 may be provided as a unitary part of the particulate air filter 141, 142. The inner layer 190 may further extend the life cycle of the respirator 100 by protecting the filter media during disinfection, cleaning, and/or sterilization processes. The inner layer 190 is composed of, for example, a flexible mesh fabric. Exemplary materials for the inner layer 190 include, but are not limited to, polyolefin, polypropylene, polyethylene, and/or polyphenylsulfone. Other flexible materials are also possible. The inner layer 190 may be removably attached to the filters 141, 142, permanently attached to the filters 141, 142, filter overmolded, or could be a stand-alone part.

In some embodiments, the respirator 100 may further include a speech diaphragm, microphone and/or a wireless transmitter to allow a user to communicate better.

Figure 4:
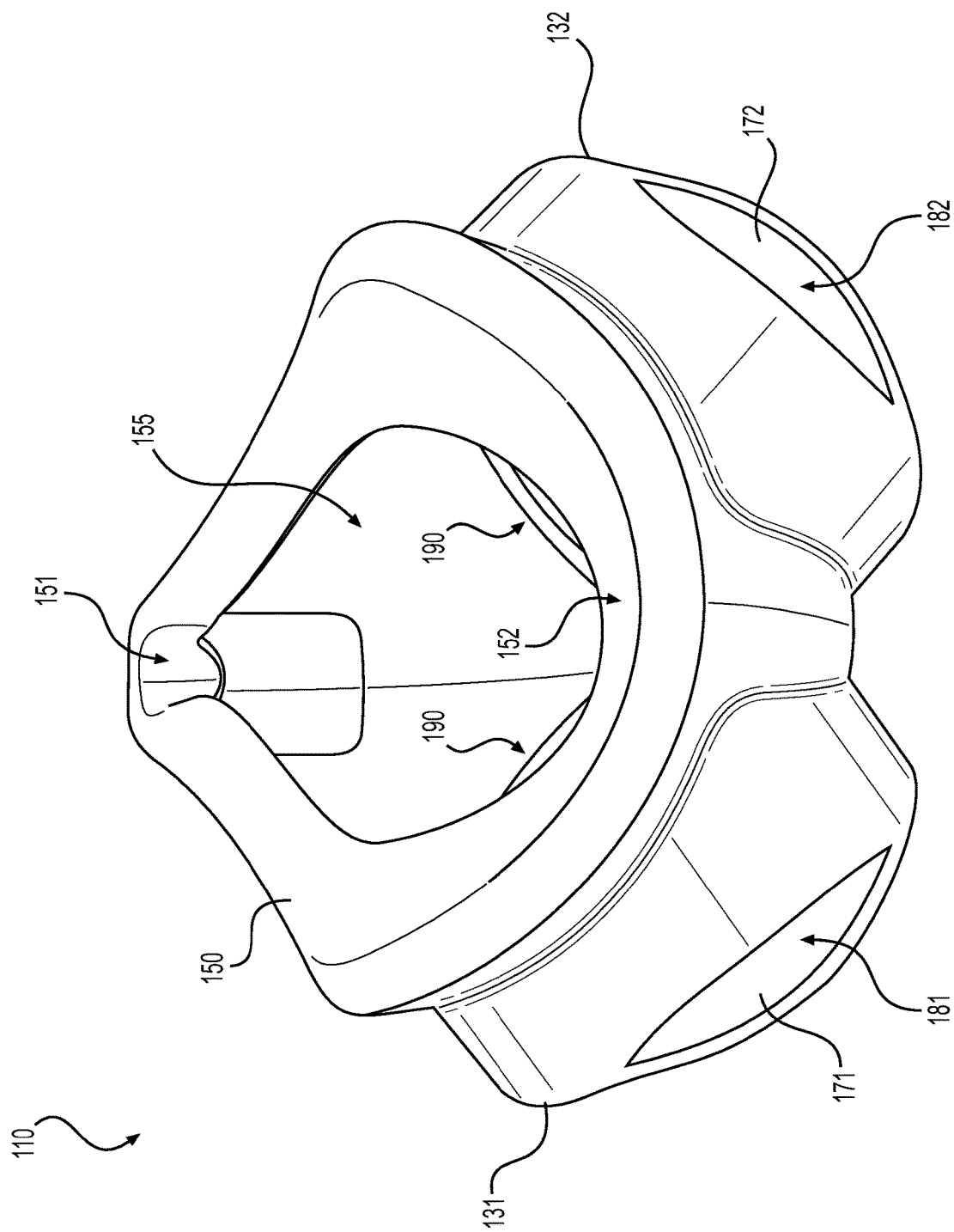
FIG. 4 is a perspective backside view of a mask of the reusable respiratory protection device of FIG. 1.

FIG. 4 is a perspective backside view of mask 110 of respirator 100. Upper and lower 161, 162 straps are not shown for clarity of illustration. The face seal 150 is adapted to comfortably fit over the user's nose and mouth and form an airtight seal against the user's face. The face seal 150 includes a main pocket 155 that encloses the user's nose and mouth and permits ample air exchange with the first and second particulate air filters 141, 142.

The face seal 150 includes a nose bridge 151 adapted to extend over the bridge of the user's nose and a chin pocket 152 adapted to extend below the user's chin, which provide the face seal 150 with a positive location that is stabilized by the lower strap 162 to ensure seal integrity. The outer profile of the face seal 150 is compact below the nose so as to reduce interference with the user's field of vision and to avoid interference with eyewear (e.g., glasses) or other personal protective equipment (e.g., face shield). The face seal 150 is adapted to fit a large variety of different face sizes and shapes. The mask 110, including the face seal 150, may be manufactured in a variety of sizes (e.g., infant, child, small, medium, large, etc.) to provide proper fit for different head sizes ranging from pediatric to adult head sizes. In certain embodiments, the face seal 150 is made of silicone or thermoplastic elastomer and is adapted to reduce facial discomfort. In some embodiments, other conformable materials may be used for the face seal 150.

Figure 6:
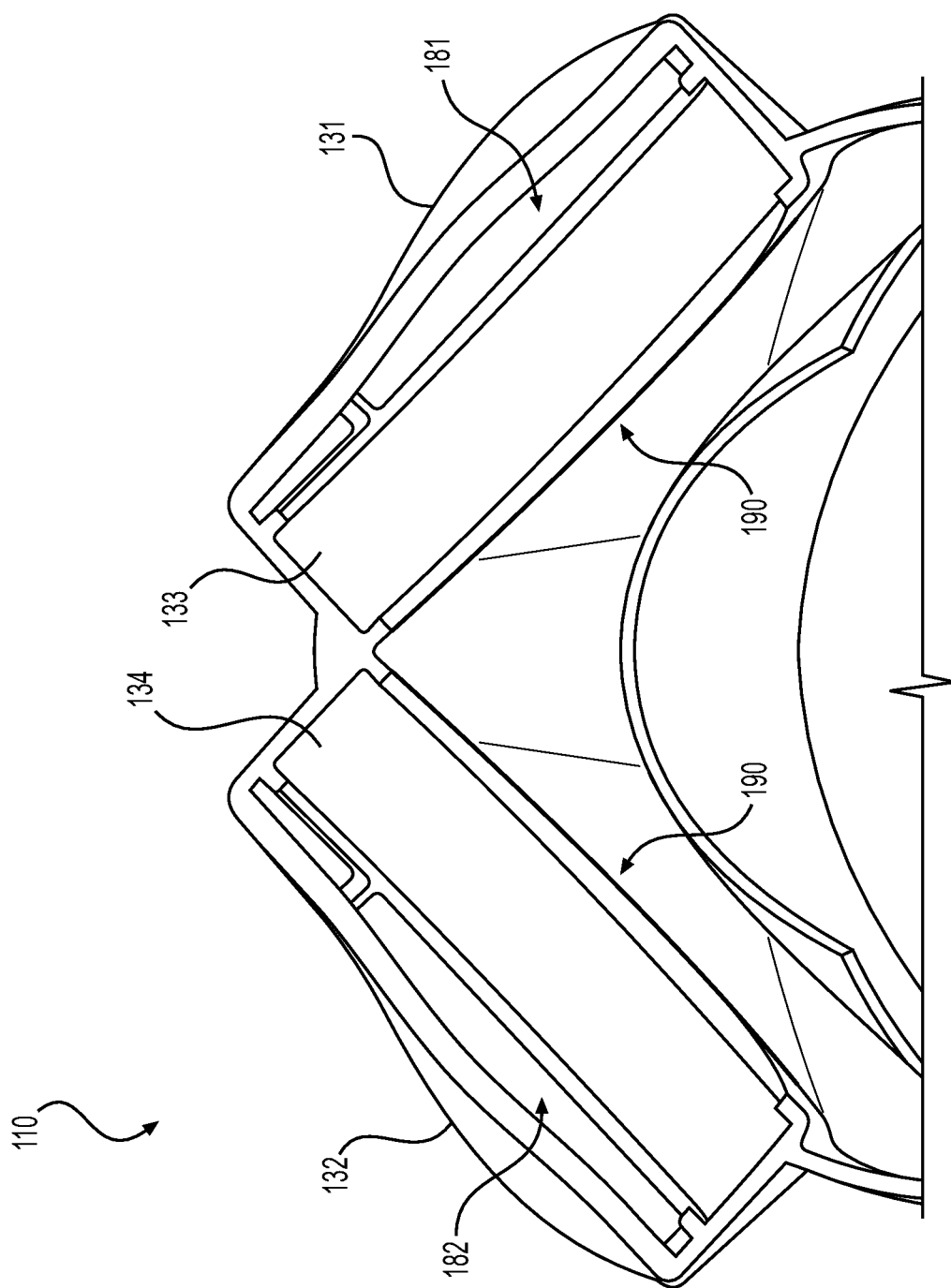
FIG. 6 is another cross-sectional bottom view of the mask of the reusable respiratory protection device of FIG. 1.

FIG. 5 is a cross-sectional bottom view of the mask 110 that shows the first and second particulate air filters 141, 142, which are located internally within the first and second outer shield portions 131, 132 of the mask 110. FIG. 6 is a cross-sectional bottom view of the mask 110 with the first and second particulate air filters 141, 142 shown removed. FIGS. 5 and 6 are best viewed together with the following description.

A first protective pocket 133 houses the first particulate air filter 141, and a second protective pocket 134 houses the second particulate air filter 142. The first and second protective pockets 133, 134 are formed within the first and second outer shields, 131, 132, respectively.

A first gap 181 is formed between the first outer shield portion 131 and the first particulate air filter 141, as depicted in FIGS. 5 and 6. Similarly, the second outer shield portion 132 is shaped to form a second gap 182 between the second outer shield 132 and the second particulate air filter 142. The first and second gaps 181, 182 provide ample space to disperse flow of air evenly across the surface of each of the particulate air filters 141, 142, which ensures efficient filter media utilization and low resistance to air flow. The first gap 181 extends to the first vent 171 (e.g., see FIG. 4) to connect the air passage to the outside. Similarly, the second gap 182 extends to the second vent 172 (e.g., see FIG. 4), to connect the air passage to the outside. In one embodiment, the first vent 171 and the second vent 172 are formed of a flexible material so as to be selectively closeable. Alternatively, in another embodiment, the vents 171, 172 may be a rigid opening in the outer surface of the mask for allowing airflow therethrough.

In operation, as a user of respirator 100 inhales, air is drawn into the mask 110 via the first and second vents 171, 172, through respective first and second gaps 181, 182, and across respective first and second particulate air filters 141, 142. Particles in the air are filtered by the first and second particulate air filters 141, 142, and purified air is delivered to the main pocket 155 within mask 110 for inhalation by the user. When exhaling, the exhaled breath of the user passes in the opposite direction through the air filters 141, 142 across the gaps 181, 182, and out of the mask 110 via the vents 171, 172.

The mask 110 includes a built-in user seal check method adapted for the user of the respirator 100 to ensure facial seal integrity with the mask 110. The user seal check method allows the user of the respirator 100 to test that the face seal 150 provides a proper airtight seal before using the respirator 100 in the field. Along an underside of the first and second outer shield portions 131, 132, where the first and second vents 171, 172 are formed, the mask 110 is adapted to be flexible, thus enabling temporary closure of the vents.

To test the seal, the outer shield portions 131, 132 can each be deflected inward against the outer surface of the mask 110 to temporarily close the closeable vents 171, 172. Specifically, the user presses inwardly (e.g., with a finger) on the outer-lower region of the first outer shield portion 131 in such a manner that the first vent 171 closes. Similarly, the user presses inwardly (e.g., with another finger) on the outer-lower region of the second outer shield portion 132 in such a manner that the second vent 172 closes. With both of the vents 171, 172 simultaneously closed, the user inhales, and if a proper airtight seal is formed, a slight inhalation vacuum results, which pulls the mask against the user's face confirming a proper facial seal. Otherwise, if a leak exists along the face seal 150, the user can detect the leak as air rushes in against the user's face and a lack of vacuum upon inhalation. Upon release of the lower region of the first and second outer shield portions 131, 132, the first and second vents 171, 172, respectively, return to their original shape. This re-opens the vents 171, 172, providing ports for air exchange with the first and second particulate air filters 141, 142, respectively.

Figure 7:
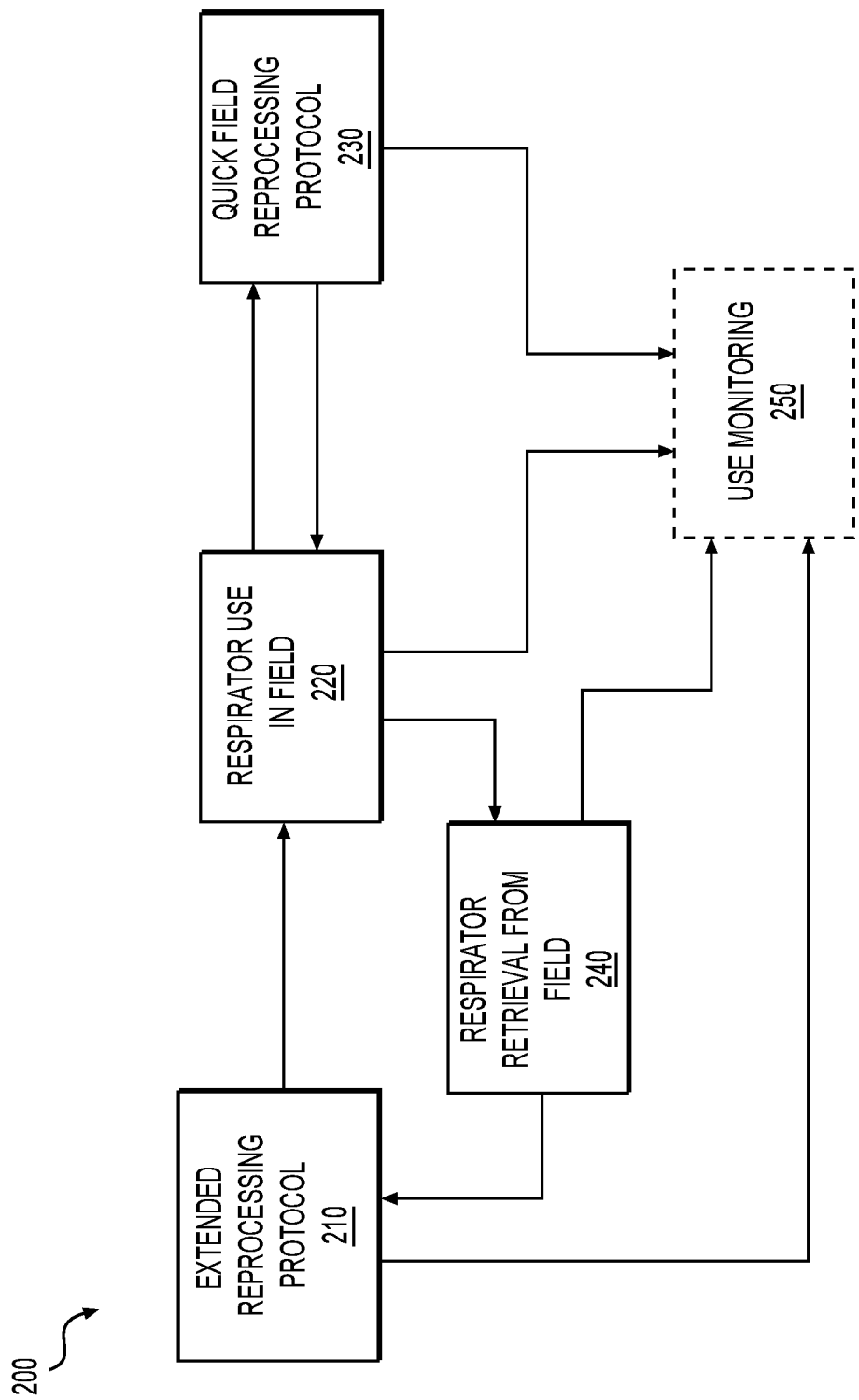
FIG. 7 is a flow diagram of a respirator reuse method for a reusable respiratory protection device, in an embodiment.

FIG. 7 is a flow diagram of an exemplary respirator reuse method 200 adapted for reuse of respirator 100 or respirator 300 (see FIGS. 8 and 9 and their description below). Respirators 100 and 300 are adapted for cleaning, disinfection, and/or sterilization using a variety of protocols, which may be employed in various combinations to increase the number of reuses, as described below in connection with FIG. 7. Although the below protocols are discussed with respect to respirator 100, similar protocols could be performed on respirator 300.

Embodiments may include performing a high-level sterilization process that includes cleaning the respirator 100 followed by autoclave treatment. Other sterilization processes such as vaporized hydrogen peroxide, ethylene oxide, gamma irradiation, etc. are envisioned. Embodiments may include performing a disinfection process that includes cleaning the respirator 100 followed by disinfection via washer-disinfector, chemical disinfection, heat disinfection, etc. Embodiments may include performing a quick field reprocessing protocol, which may include manually cleaning and disinfecting the respirator 100, 300 by an operator or assigned staff.

More specifically, in Step 210, an extended reprocessing protocol is performed. In one embodiment, the extended reprocessing protocol 210 involves cleaning, disinfecting and/or sterilizing steps using specialized equipment that may be found in a hospital or other health care setting, such as an autoclave, washer-disinfector, gamma radiation, VHP, EtO, ultrasonic bath, etc. The respirator 100 is adapted to be fully autoclavable, cleanable, and/or disinfectable as a single unit (e.g., without requiring any disassembly and reassembly), including with the first and second particulate air filters 141, 142, as well as with the upper and lower straps 161, 162 attached.

In certain embodiments, the first and second particulate air filters 141, 142, as well as the upper and lower straps 161, 162 may be disassembled and processed separately using the extended reprocessing protocol of Step 210. In an example of Step 210, the respirator 100 is subjected to a cleaning and/or disinfecting step in a washer-disinfector at about >50° C. or an ultrasonic bath after retrieval from the field (see Step 240, described below); and then following washing/cleaning/disinfecting, the respirator 100 is subjected to autoclaving (e.g., steam sterilization application of high temperature and pressure) for a predetermined duration. The order of the cleaning/disinfecting and autoclaving steps may be reversed in some embodiments. In some embodiments, a pre-rinse to the respirator may be included. An exemplary extended reprocessing protocol is an OSHA protocol defined under 29 CFR 1910.134. Another embodiment of the cleaning and sterilization process allows the respirator to be disassembled and each part undergoes a separate cleaning and sterilization process.

As an alternative to above-described processing methods, the extended reprocessing protocol 210 may include cleaning and drying the respirator 100 at home for personal reuse using a washing machine or dishwasher, and then a residential dryer if necessary.

Reuse of the filter media following cleaning/disinfection/sterilization processing is an advantage for the reusability of the respirator 100. A greater number of reuses provides a lower cost per use, reduces the need for stockpiling of respirators in preparation for a pandemic, and maintains availability of clean respirators during a pandemic. In certain embodiments, the extended reprocessing protocol of Step 210 enables safe reuse of respirator 100 for at least one hundred reuses.

In Step 220, the respirator 100 is used in the field. In an example of Step 220, the respirator 100 is deployed for use in the field after extended reprocessing protocol 210. In another example of Step 220, the respirator 100 is deployed for use in the field after a quick field reprocessing protocol is performed (see Step 230, described below). Here the term "field" is meant to broadly include any indoor or outdoor location where the respirator 100 may be worn by a user, including but not limited to hospitals, clinics, other occupational settings, homes, businesses, parks, gyms, and while traveling via transportation vehicles (e.g., airplanes, ships, trains, automobiles, bicycles, scooters, etc.).

In Step 230, a quick field reprocessing protocol is performed. In an example of Step 230, the respirator 100 is wiped down with a disinfectant material or a disinfecting wipe. In another example of Step 230, at least a portion of the respirator 100 is cleaned with a detergent, then disinfected with a wipe or spray. In some embodiments, only the exterior surfaces of the mask 110 (including those surfaces facing the user) are cleaned/disinfected. In other embodiments, the mask 110 and straps 161, 162 are cleaned/disinfected. In some embodiments, the respirator 100 may be disinfected with isopropyl alcohol, bleach, hydrogen peroxide, or other known disinfectants. The quick field reprocessing protocol may be quickly performed (e.g., in less than one minute) without needing specialized cleaning equipment such as an autoclave, washer-disinfector, or ultrasonic bath. The quick field reprocessing protocol is intended to be performed a predetermined number of times (e.g., five or more) to provide a limited number of reuses before performing the extended reprocessing protocol referenced in Step 210.

The quick field reprocessing protocol may include steps intended to ensure adequate disinfection based on standard-operating-procedures that adhere to tested and well-defined health care practices. For example, the quick field reprocessing protocol may stipulate an appropriate disinfectant, a preferred sequence of surfaces to wipe, a sufficient duration for wiping and a sufficient contact time of the disinfectant. The quick field reprocessing protocol may stipulate steps for the safety of the person performing the protocol, such as instructions for wearing safety gloves, a lab coat, safety glasses, etc. Additionally, the quick field reprocessing protocol may stipulate steps for appropriate disposal of the wipes (e.g., instructions regarding local regulations for the handling and disposal of biohazardous waste). The quick field reprocessing protocol 230 may be performed while the respirator is worn by the user. Due to the smooth wipeable surfaces of the mask 110 and straps 161, 162, the user is able to easily wipe down the mask 110 prior to donning and doffing to mitigate self-contamination.

Following Step 230, the respirator reuse method 200 returns to Step 220 for reusing the respirator in the field. The respirator reuse method 200 is intended to proceed back and forth between Step 220 and Step 230 a limited number of times before the respirator reuse method 200 proceeds with Step 240, described below, for retrieval of the respirator 100 from the field. The number of uses (in Step 220) and optionally the number of subsequent quick field reprocessing protocols (in Step 230) that are performed in between extended reprocessing protocols (in Step 210) may be tracked as part of a use monitoring program, as further described below in connection with Step 250. Alternatively, the respirator reuse method may be performed without Step 230 entirely.

When Step 210 and Step 230 are both performed, the number of quick field reprocessing protocols between each extended reprocessing protocol results is a multiplier of the available number of uses. For example, if the respirator 100 is processed by the quick field reprocessing protocol 230 five times between each extended reprocessing protocol 210, the respirator 100 would be then be able to be used six hundred times rather than one hundred.

In Step 240, the respirator is retrieved from the field. The respirator may be retrieved from the field after a predetermined number (e.g., five) of quick-field disinfections, or fewer/longer, as performed in Step 230. In an example of Step 240, a health care worker turns in their respirator 100 to a health care facility equipped with specialized equipment for performing an extended reprocessing protocol in Step 210. In an example of Step 240 for personal use, a user places the respirator 100 in a home dishwasher or home washing machine for cleaning in Step 210.

In an optional Step 250, monitoring the use and reprocessing of the respirator is performed for the purposes of life cycle management. In an example of Step 250, the respirator 100 is tracked as part of a use monitoring program. An identification tag 105, shown in FIGS. 2 and 3, may be attached to the respirator 100 for quickly identifying individual respirators as part of the use monitoring program. An example of the identification tag 105 is a scannable identification tag, including but not limited to a barcode or a radio-frequency identification (RFID) tag, which may be scanned with a scanning device for quickly identifying a respirator 100 and indicating its current use category. The barcode may be a one-dimensional (1D) barcode, a two-dimensional (2D), or a matrix barcode such as a Quick Response (QR) code. Alternatively, a RFID tag may be attached to, or embedded within, the respirator 100 for identifying each respirator unit (e.g., via a serial number)

and for tracking its use and disinfection. Other types of tracking devices or markers 105 may also be used.

For example, in connection with Step 210, following completion of the extended reprocessing protocol, or optionally at intermediate steps throughout the reprocessing protocol, individual respirators 100 are scanned for tracking their status via a processor within a database. Use monitoring may be performed in connection with any of the steps of the respirator reuse method 200. For example, following each use in the field (Step 220), and/or following each quick field reprocessing protocol (Step 230), and/or following each extended reprocessing protocol 210, and/or following retrieval of the respirator (Step 240), respirator 100 may be scanned for updating the database accordingly. The database may also be accessed from a mobile device (e.g., smartphone or tablet) for remotely updating information (e.g., to indicate that a quick field reprocessing protocol 230 has been performed in the field).

The extended reprocessing protocol 200 may be manual or automated. For example, batch processing of a plurality of respirators may be accomplished by a machine-automated process.

Figure 8:
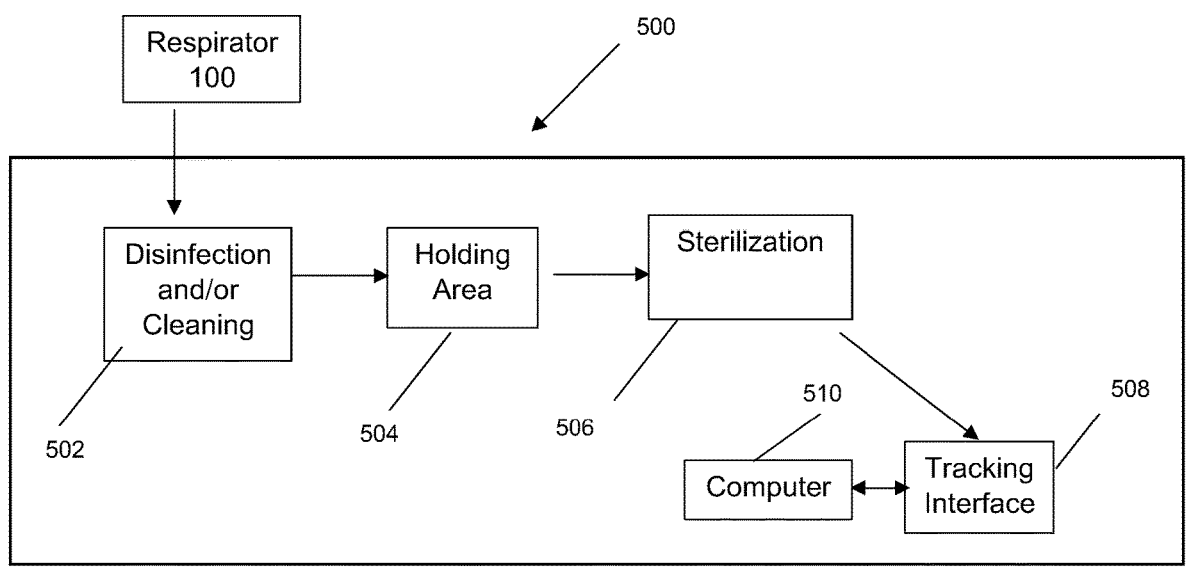
FIG. 8 shows a machine that is designed to receive the respirator for performing the process of the invention.

FIG. 8 shows an embodiment of a machine 500 designed to receive the respirator 100 for the extended reprocessing protocol 210. Machine 500 may include a first stage 502 where disinfection/cleaning is performed, an optional holding area 504, a second stage 506 wherein sterilization is performed.

In some embodiments, the disinfection machine 500 may include a tracking interface 508 that cooperates with an identification tag 105 on the respirator to indicate that a disinfection cycle has been performed. The tracking interface 508 may cooperate with a computer 510 that may have at least one processor, a graphical user interface, an input device, and a display for allowing the user to track the disinfection process. Tracking may include the number of times the disinfection has been performed on the particular personal protective equipment (PPE), the locations where the PPE has been used, and the identification of users of the PPE. The computer 510 may optionally interface with an inventory management system for assisting with inventory management and purchasing.

The computer 510 may also allow a user to control all aspects of the process, including the predetermined amounts of time for each of the steps, the desired concentrations for any disinfecting solutions being applied, a temperature for sterilization, and the type of sterilization to be applied. The machine 500 is capable of processing one respirator or a plurality of respirators simultaneously. The machine 500 may include a bar-code reader or other scanner or tracking device for receiving information from each respirator to be treated, which may be read from an indicator, such as identification tag 105.

For purposes of life cycle management of the respirator, the machine 500 may manually receive the age of the respirator from the operator or may automatically detect the age of the respirator. The machine 500 may include an automatic detection mechanism for determining the age of the respirator, such as by a spectral scan of the material, a measurement of the off-gassing or volatile materials, or a particular response to the disinfection process. The machine 500 may alternatively or additionally detect the age of the PPE from identification tag 105 on the respirator, which may be cross-referenced with a database tracking system. The machine 500 may alternatively or additionally use the identification tag 105 to correlate the number of allowable disinfection cycles with a look-up table containing the useful life for various respirator and contamination levels/types. The machine 500 may include a mechanism for providing an alert, which may be visual and/or audio, when the respirator has exceeded the allowable number of disinfection cycles.

The disinfection machine 500 may include racks designed to support the respirator such that all outer surfaces can be evenly treated during the process. The racks may be extendable and/or interchangeable depending on what type/size of respirator is to be disinfected. The machine 500 may include hooks for hanging the straps of the respirator thereon.

In some embodiments, central computer 510 that is part of machine 500 described in reference to FIG. 8 may be a computer 702 as described with reference to FIG. 9.

Figure 9:
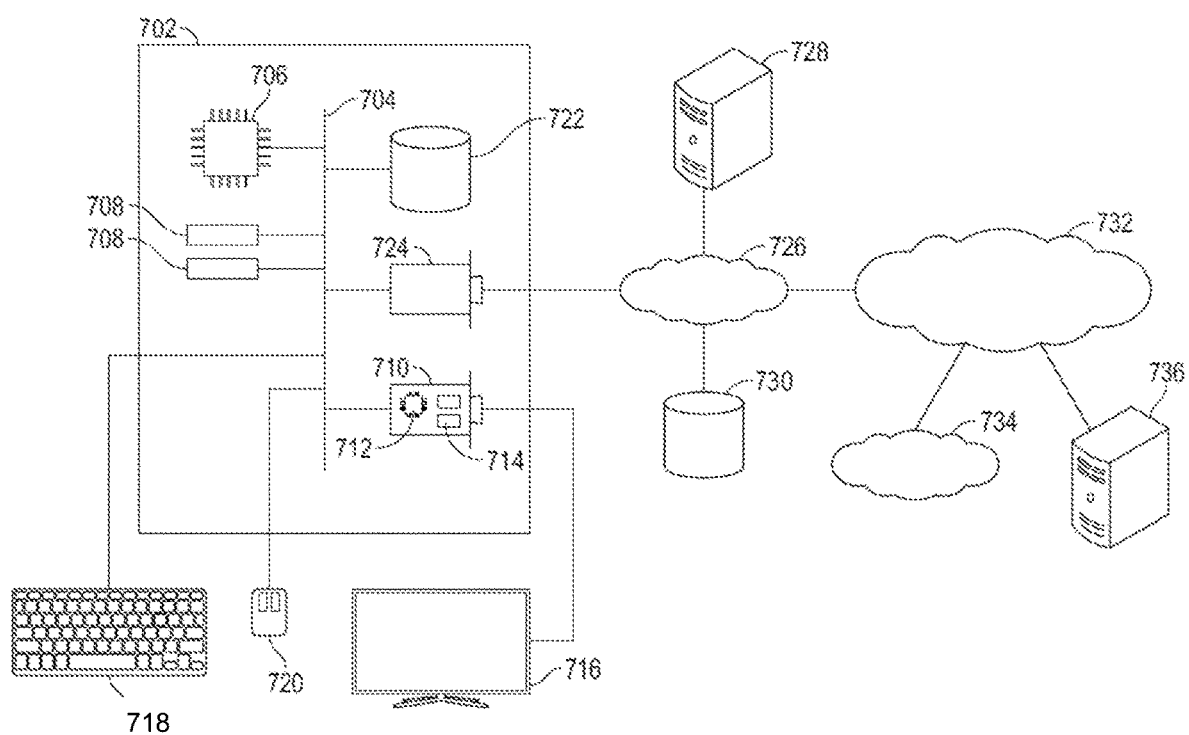
FIG. 9 shows an exemplary hardware platform for certain embodiments of the invention.

FIG. 9 shows an exemplary hardware platform for certain embodiments of the invention. Computer 702 can be a desktop computer, a laptop computer, a server computer, a mobile device such as a smartphone or tablet, or any other form factor of general- or special-purpose computing device. Depicted with computer 702 are several components, for illustrative purposes. In some embodiments, certain components may be arranged differently or absent. Additional components may also be present. Included in computer 702 is system bus 704, whereby other components of computer 702 can communicate with each other. In certain embodiments, there may be multiple busses or components may communicate with each other directly. Connected to system bus 704 is central processing unit (CPU) 706. Also attached to system bus 704 are one or more random-access memory (RAM) modules 708. Also attached to system bus 704 is graphics card 710. In some embodiments, graphics card 710 may not be a physically separate card, but rather may be integrated into the motherboard or the CPU 706. In some embodiments, graphics card 710 has a separate graphics-processing unit (GPU) 712, which can be used for graphics processing or for general purpose computing (GPGPU). Also on graphics card 710 is GPU memory 714. Connected (directly or indirectly) to graphics card 710 is display 716 for user interaction. In some embodiments, no display is present, while in others it is integrated into computer 702. Similarly, peripherals such as keyboard 718 and mouse 720 are connected to system bus 704. Like display 716, these peripherals may be integrated into computer 702 or absent. Also connected to system bus 704 is local storage 722, which may be any form of computer-readable media and may be internally installed in computer 702 or externally and removably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-usable instructions, data structures, program modules, and other data representations.

Finally, network interface card (NIC) 724 is also attached to system bus 704 and allows computer 702 to communicate over a network such as network 726. NIC 724 can be any form of network interface known in the art, such as Ethernet, ATM, fiber, Bluetooth, or Wi-Fi (i.e., the IEEE 802.11 family of standards). NIC 724 connects computer 702 to local network 726, which may also include one or more other computers, such as computer 728, and network storage, such as data store 730. Generally, a data store such as data store 730 may be any repository from which information can be stored and retrieved as needed. Examples of data stores include relational or object-oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 728, accessible on a local network such as local network 726, or remotely accessible over Internet 732. Local network 726 is in turn connected to Internet 732, which connects many networks such as local network 726, remote network 734 or directly attached computers such as computer 736. In some embodiments, computer 702 can itself be directly connected to Internet 732. Additionally, instructions to perform any of the steps described in reference to FIG. 7 may be stored on the local storage 722.

Figure 10:
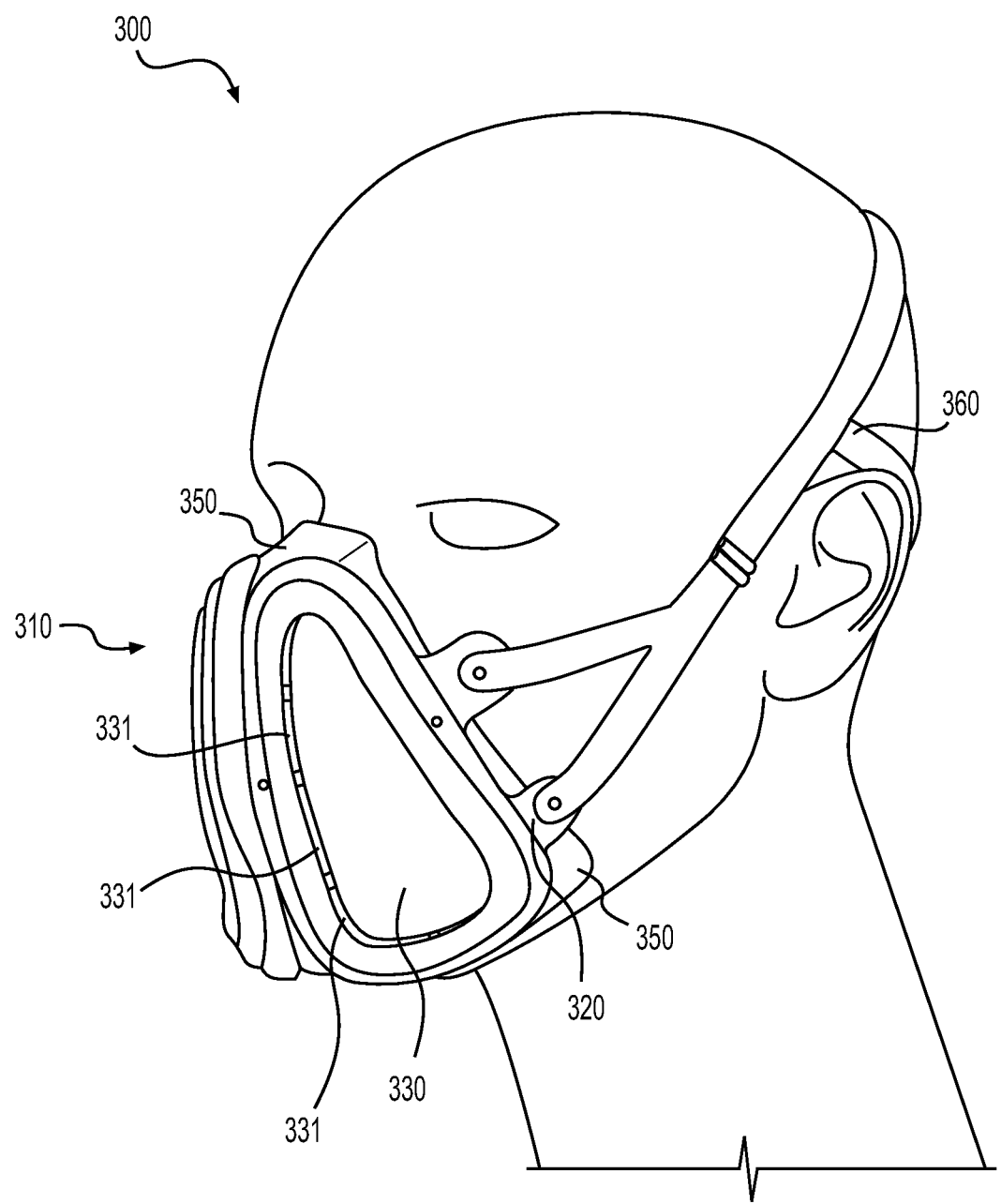
FIG. 10 shows a second embodiment of a reusable respiratory protection device.

FIG. 10 shows a second embodiment of an exemplary reusable respiratory protection device 300 having a mask 310 and a strap 360. The reusable respiratory protection device 300 may be referred to herein as "respirator 300" for short. The respirator 300 may be similar to respirator 100, FIG. 1. For example, the mask 310 is also a half mask that covers the lower portion of the user's face including the nose and mouth but not the eyes. The respirator 300 is also adapted to be lightweight for improved comfort (e.g., between about 3-oz. to about 4-oz).

A frame 320 provides structural support for other components and one or more attachment points for the strap 360. A pair of outer shield portions 330 each serve as a splashguard that protect an inner filter material, such as particulate air filters 340 (see FIG. 9) from contamination. Each outer shield portion 330 is positioned on one side (e.g., left or right) of the mask 310. A plurality of vents 331 are positioned along the edge of each outer shield portion 330 for allowing air passage to and from the particulate air filters 340. Not all vents 331 are enumerated in FIGS. 10 and 11 for clarity of illustration. The outer shield portions 330 are compatible with reprocessing protocols, such as the quick field reprocessing protocol 230, described above in connection with FIG. 7. A face seal 350 provides an airtight seal against the wearer's face.

Figure 11:
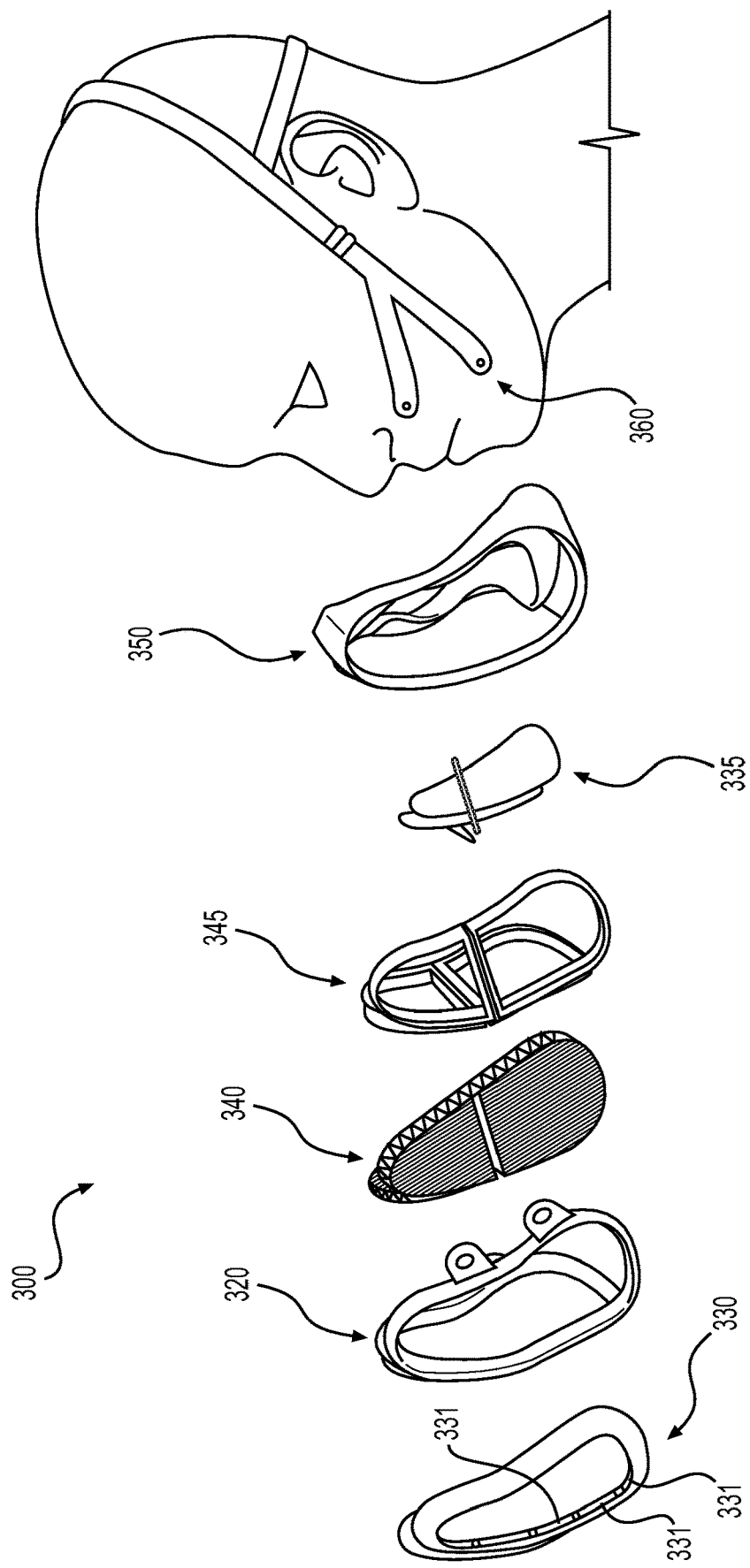
FIG. 11 is an exploded view showing components of the reusable respiratory protection device of FIG. 10.

FIG. 11 shows an exploded view of the respirator 300 of the embodiment of FIG. 8. The exploded view provides separation between components of the respirator 300 for clarity of illustration. In addition to the components depicted in FIG. 10, FIG. 11 illustrates a particulate air filter 340 and a filter rim 345 adapted for holding the particulate air filters 340. An optional inner shield 335 may be used in some embodiments for protecting an inner side of the particulate air filters 340, as further described below. In certain embodiments, the particulate air filters 340 may include a pair of air filters 340 each adapted for a left and right side of mask 310, respectively. Likewise, the optional inner shield 335 may include a pair of inner shields 335 each adapted for a respective side of mask 310.

The face seal 350 includes a nose bridge that extends over the bridge of the wearer's nose and a chin pocket that extends below the wearer's chin, which provide the face seal 350 with a positive location that is stabilized by the strap 360 to ensure seal integrity.

In certain embodiments, the frame 320 includes a pair of frames each adapted for supporting one of the pair of particulate air filters 340 and one of the pair of outer shield portions 330, respectively. However, in some embodiments, the frame 320 is molded as a single component. During manufacture of the mask 310, the filter rim 345 is overmolded with the frame 320 encapsulating the particulate air filters 340. The outer shield portions 330 are coupled with the frame 320 (e.g., overmolded or snap-in) for protecting the outer side of the particulate air filters 340.

The outer shield portions 330 include a substantially smooth surface adapted for protecting the particulate air filters 340 and for being wettable and washable. Each outer shield portion 330 is raised above the particulate air filter 340 creating a gap between the outer shield portion 330 and the frame 320 with an ample plenum incorporated on the underside of the outer shield portion 330 to disperse flow evenly across the surface of the particulate air filters 340 ensuring efficient filter media utilization and low resistance. The plurality of vents 331 provide ports for passage of air from outside the respirator 330 to the space behind each outer shield 330.

Each outer shield portion 330 provides a semi-rigid protective surface for covering the underlying particulate air filter 340. An exemplary material for the outer shield portion 330 is silicone. The outer shield portion 330 is also wettable and resistant to common disinfectants, such as benzalkonium chloride, hypochlorite or quaternary amines, for example.

In general, during wash and disinfecting cycles, mechanical stress placed on filter media when fully exposed to the forces of the washing cycle reduce the filter media life. The outer shield portions 330 not only provide protection from biological fluid contamination (e.g., blood, saliva, and cough/sneeze droplets), the outer shield portions 330 also increase the number of wash cycles that the underlying particulate air filters 340 can withstand, extending the life cycle of the respirator 300. The outer shield portion 330 also enables a simplified cleaning process, including automated cleaning regimens.

The particulate air filter 340 may be similar to the first particulate air filter 141 of FIG. 3. The filter rim 345 is configured to hold at least one particulate air filter 340. In some embodiments, the filter rim 345 is adapted to hold a pair of particulate air filters 340, one on the left side of the mask 310 and another on the right side of the mask 310. In some embodiments, the filter rim 345 is adapted to encapsulate four particulate air filters 340, a top-left, a top-right, a bottom-left, and a bottom-right particulate air filter. Other configurations of the filters are possible.

The filter rim 345 and the frame 320 may be molded separately or overmolded together in one step with one or more particulate air filters 340 encapsulated therein. In certain embodiments, each particulate air filter 340 includes a polytetrafluoroethylene (PTFE) filter media having at least one layer of PTFE. In some embodiments, the particulate air filter 340 may include other types of filter media, such as high-efficiency particulate air (HEPA) filters and ultra-low particulate air (ULPA) filters. Other types of filter media such as microglass may be used without departing from the scope hereof, although a non-shedding filter media is preferable for durability.

Similar to the first and second particulate air filters 141, 142, the particulate air filter 340 is adapted to exceed NIOSH requirements for the N95 filter class after performing numerous reprocessing protocols. The thickness of the particulate air filter 340 is adapted to be thin enough for improved ventilation, lower breathing resistance, and speech intelligibility.

The optional pair of inner shields 335 provide a washable, flexible insert (e.g., a scrim) that provides a protective surface covering the pair of particulate air filters 340, respectively. The optional inner shields 335 extend the life cycle of the respirator by protecting the filter media during automated cleaning processes.

The face seal 350 is similar to the face seal 150 of FIG. 1 and designed to comfortably fit over the wearer's nose and mouth and form an airtight seal. In certain embodiments, the face seal 350 is made of silicone and is adapted to reduce facial pressure and discomfort.

The face seal 350 includes a built-in user seal check method. The user seal check method is adapted for a wearer of the respirator 300 to test that the face seal 350 provides a proper airtight seal. In one embodiment, the pair of outer shield portions 330 are each adapted to be collapsible against a respective particulate air filter 340, providing a seal against the respective air filter 340, which allows the user seal test to be performed. Each outer shield portion 330 is flexible enough to be pushed into a collapsed configuration to create a seal when needed. The user then tests the seal by inhaling slightly to confirm a good facial seal. A flap valve may be included on the mask 310 that is activated by a push of a finger. The flap valve is normally slightly open and may be pushed closed with a finger. The user then tests the seal by inhaling slightly to confirm a good facial seal.

The materials used to form the individual components of the respirator 300 are selected to have bonding compatibility with one another to ensure a durable bond. For example, the outer shield portion 330, frame 320, filter rim 345, optional inner shield 335, and face seal 350 may be made of one or more plastic materials (e.g., via an injection molding process) that have bonding compatibility (e.g., for overmolding). Exemplary plastic materials include but are not limited to silicone, polypropylene, Thermoplastic Silicone Vulcanizate (TPSiV), polyolefin, polyphenylsulfone, high-density polyethylene (HDPE), acrylonitrile butadiene styrene (ABS), acrylic polymethyl methacrylate (acrylic PMMA), acetal copolymer (POM), polyetheretherketone (PEEK), and/or polybutylene terephthalate (PBTR).

In certain embodiments, the strap 360 provides a single-sized harness made of a single piece of material (e.g., a silicone material). Alternatively, the strap 360 may include a two-piece harness, or multiple pieces. The strap 360 may be available in different sizes to fit different head sizes of the user. The strap 360 is adapted to avoid the wearer's ears to prevent hearing impairment. The strap may be coupled to the frame 320 in an integrated or detachable manner.

Respirator 300 is adapted to be lightweight for improved comfort, especially for health care workers who may wear a respirator for long durations. For example, the respirator 300 is adapted to be lighter than existing elastomeric half-mask respirators due to the use of lighter materials and fewer materials. In certain embodiments, the mask weighs between about 3-oz. to about 4-oz, but may weigh more or less. The respirator 300 is adapted to have a shelf life longer than that of existing N95 FFRs, which is typically three to five years, due to the use of materials that last longer. In certain embodiments, the rated shelf life of respirator 300 is expected to be greater than fifteen years.

Respirator 300 may include an identification tag similar to the identification tag 105 described above in connection with FIGS. 2 and 3. Respirator 300 may be used with respirator reuse method 200 described above in connection with FIG. 7.

Advantages provided by embodiments of this disclosure include the ability to clean, disinfect, and/or sterilize the respirator 100 as a single unit (including filtration media) without disassembly using either automated reprocessing technologies found in health care settings, other occupational settings, or homes and/or manual field reprocessing protocols (e.g., OSHA cleaning/disinfection guidance, disinfectant wipe, etc.) that can be performed regardless of environment. The materials used to construct the respirator 100 can withstand temperatures in excess of 50° C. These features foster reusability especially in the health care setting, which leads to a lower cost per use and reduced storage requirements compared to current N95 FFRs used in health care settings. In addition to filtering particles, gas/vapor absorbents (e.g., carbon) may be added to the respirator to provide VOC capture.

Another advantage is an increased lifetime of the respirator 100 compared to FFRs and possibly HMERs and/or their filters, both in terms of years and total uses, because of the materials selected and the exclusion of any adhesive bonds between components that are susceptible to premature failure, especially when repeatedly subjected to harsh cleaning treatments (e.g., disinfectants, autoclaving, washer-disinfection, and/or ultrasonic bath). A longer shelf life also leads to lower costs for the user.

The reusable respirator 100, 300 is designed to limit bioburden accumulation by using smooth external surfaces. Because the mask 110 (and potentially straps 161, 162) is formed from a single piece of material, creases, bond lines, and other non-smooth surfaces that typically exist along interfaces between separate components are mitigated. This provides an advantage for cleanability, since smooth surfaces are more readily wiped clean. These smooth surfaces help facilitate the use of a quick field reprocessing protocol (e.g., disinfectant wipe) that may be applied for a limited number of reuses (e.g., five or more) between disinfection processing, which increases the total number of reuses (e.g., >600 total reuses). Bioburden is also mitigated by providing an external surface shape with easy accessibility that reduces entrapment geometry where bioburden can accumulate. All external surfaces are elastomeric and smooth making manual wiping effective at removing contamination.

Other advantages are the use of an integrated tracking feature (e.g., barcode, QR code, or RFID tag) for monitoring reuse. The disclosed embodiments do not require exhalation valves, which are commonly used in FFRs and HMERs and disadvantageously allow the user to breathe out contaminants, making these devices unacceptable for use in a sterile environment such as an operating room. Although the disclosed embodiments are adapted for use in health care settings, they also provide an improved reusable respirator option for the general public to protect themselves against airborne particulate threats.

Features described above as well as those claimed below may be combined in various ways without departing from the scope hereof. The following examples illustrate some possible, non-limiting combinations:

(A1) A reusable respiratory protection device includes a mask adapted for covering a portion of a user's face. The mask includes a face seal adapted to conform to a user's face around a nose and a mouth of the user, an outer surface, at least one outer shield portion formed in the outer surface, and at least one closeable vent through the at least one outer shield portion. The reusable respiratory protection device further includes at least one particulate air filter adapted to filter at least 95% of airborne particles. The at least one particulate air filter is housed within the at least one outer shield portion. The at least one closeable vent is adapted to direct air flow through the outer surface for filtering by the at least one particulate air filter. The outer surface is substantially smooth to mitigate bioburden accumulation and wettable to allow for cleaning, disinfection, or sterilization thereof. A strap is configured to secure the mask to the user's face.

(A2) For the reusable respiratory protection device denoted as (A1), the device may be configured to be cleaned, disinfected, and sterilized without disassembly to facilitate reuse.

(A3) For the reusable respiratory protection device denoted as (A1) or (A2), the device may be configured to be sterilized by autoclaving, gamma irradiation, vaporized hydrogen peroxide, or ethylene oxide.

(A4) For the reusable respiratory protection device denoted as any of (A1) through (A3), the device may be configured to be cleaned, disinfected, or sterilized at temperatures above about 50° C. to facilitate reuse.

(A5) For the reusable respiratory protection device denoted as any of (A1) through (A4), the mask may be a unitary structure formed of a single piece of material.

(A6) For the reusable respiratory protection device denoted as any of (A1) through (A5), a protective pocket may be formed in each of the at least one outer shield portion, the protective pocket being adapted to protect the at least one particulate air filter, thereby permitting cleaning and disinfecting of the outer surface.

(A7) For the reusable respiratory protection device denoted as any of (A1) through (A6), the strap and the mask may be made of a silicone material that is configured to be cleaned, disinfected, and sterilized to facilitate reuse.

(A8) For the reusable respiratory protection device denoted as any of (A1) through (A7), the at least one particulate air filter may include a filter media having at least one polytetrafluoroethylene-based layer that is wettable and sterilizable.

(A9) For the reusable respiratory protection device denoted as any of (A1) through (A8), the at least one outer shield portion may be deformable for enabling closure of the at least one closeable vent for functional testing of the face seal during use.

(A10) For the reusable respiratory protection device denoted as any of (A1) through (A9), the at least one outer shield portion may form a gap between the outer surface of the mask and the at least one particulate air filter that extends to the at least one closeable vent, the gap being adapted to provide ample space for dispersing flow of air evenly across the surface of the at least one particulate air filter.

(A11) For the reusable respiratory protection device denoted as any of (A1) through (A10), an inner flexible layer disposed on an inner surface of the at least one particulate air filter, wherein the inner flexible layer is located between the at least one particulate air filter and the user during use.

(A12) For the reusable respiratory protection device denoted as any of (A1) through (A11), an identification tag may be provided, said identification tag being adapted for scanning with a scanning device.

(A13) For the reusable respiratory protection device denoted as any of (A1) through (A12), the substantially smooth outer surface may be configured to allow cleaning or disinfecting of the device while being worn by the user.

(A14) For the reusable respiratory protection device denoted as any of (A1) through (A13), the mask may have no exhalation valve such that the mask is configured to maintain a sterile field in an environment surrounding the user during use.

(B1) A reusable respirator includes a unitary mask formed of a single piece of material adapted for covering a portion of a user's face. The mask includes a face seal adapted to conform to a user's face around a nose and a mouth of the user, an outer surface, a first outer shield portion formed in the outer surface, a first vent through the first outer shield portion, a second outer shield portion formed in the outer surface, and a second vent through the second outer shield portion. A first particulate air filter, housed within the first outer shield portion, is adapted to filter at least 95% of airborne particles. A second particulate air filter, housed within the second outer shield portion, is adapted to filter at least 95% of airborne particles. The first vent and the second vent are each adapted to direct air flow to the first particulate air filter and the second particulate air filter, respectively. The outer surface of the mask is substantially smooth to mitigate bioburden accumulation and wettable to allow for cleaning, disinfection, or sterilization thereof.

(B2) For the reusable respirator denoted as (B1), the first outer shield portion may be deformable for enabling closure of the first vent, and the second outer shield portion may be deformable for enabling closure of the second vent, such that the first vent and the second vent are temporarily closeable for functional testing of the face seal during use.

(C1) A method for processing a respirator for reuse includes a) providing a reusable respirator. The reusable respirator includes a mask adapted for covering a portion of a user's face. The mask includes a face seal adapted to conform to a user's face around a nose and a mouth of the user, an outer surface, at least one outer shield portion formed in the outer surface, and at least one closeable vent through the at least one outer shield portion. At least one particulate air filter, housed within the at least one outer shield portion, is adapted to filter at least 95% of airborne particles. The at least one closeable vent is adapted to direct air flow through the outer surface for filtering by the at least one particulate air filter. The outer surface is substantially smooth and wettable to allow for disinfection thereof. A strap is configured to secure the mask to the user's face. The method further includes b) using the reusable respirator in a field, and c) performing an extended reprocessing protocol.

(C2) For the method for processing a respirator denoted as (C1), the method may comprise performing a quick field reprocessing protocol a predetermined number of times before step c).

(C3) For the method for processing a respirator denoted as any of (C1) through (C2), the respirator may further comprise an identification tag, and the method may further comprise: scanning the identification tag to track use or the respirator, processing of the respirator, or both.

(C4) For the method for processing a respirator denoted as any of (C1) through (C3), performing the extended reprocessing protocol may comprise: sterilizing the reusable respirator without disassembly.

It should be appreciated that, while the above disclosure has been generally directed to the field of respirator masks for protection from airborne particles such as bacteria and viruses, embodiments of this disclosure may be directed to other fields and uses. For example, embodiments of the elastomeric half-mask N95 reusable respirator described herein may be adapted to filter other types of particulates and to provide different levels of protection, such as 99% or 99.97% minimum filtration efficiency (e.g., N99 or N100 filter classes, respectively) or different classes (P-series, R-series). Additionally, while the respirator 100, 300 is designed for compatibility with health care worker use, this device may be used by other industry and the general population and cleaned using a home dishwasher/washing machine or other suitable methods.

Although embodiments of this disclosure have been described with reference to the illustrations in the attached drawing figures, it is noted that equivalents may be employed and substitutions made herein without departing from the scope hereof as recited in the claims.

Having thus described various embodiments, what is claimed as new and desired to be protected by Letters Patent includes the following:

1. A sterilizable respiratory protection device, comprising:
   at least one particulate air filter; and
   a unitary mask adapted for covering a portion of a user's face, said mask comprising:
      a face seal adapted to conform to a user's face around a nose and a mouth of the user;
      at least one outer shield portion forming a protrusion on an outer surface, said protrusion forming a protective pocket for housing the at least one particulate air filter; and
      at least one deformable opening formed through the at least one outer shield portion;
      wherein the at least one deformable opening is adapted to direct air flow through the outer surface for filtering by the at least one particulate air filter when open, and
      wherein the at least one deformable opening is adapted to prevent air flow through the outer surface for testing the seal when closed.

2. The sterilizable respiratory protection device of claim 1, wherein the device further comprises a plurality of straps, wherein said mask and said plurality of straps are molded as a single piece of material.

3. The sterilizable respiratory protection device of claim 1, wherein the at least one outer shield portion comprises a first outer shield portion and a second outer shield portion.

4. The sterilizable respiratory protection device of claim 3, wherein the at least one particulate air filter comprises a first particulate air filter housed within the protective pocket of the first outer shield portion and a second particulate air filter housed within the protective pocket of the second outer shield portion.

5. The sterilizable respiratory protection device of claim 1, wherein the at least one particulate air filter is adapted to filter at least 95% of airborne most penetrating particles.

6. The sterilizable respiratory protection device of claim 1, wherein the outer surface is substantially smooth to mitigate bioburden accumulation.

7. The sterilizable respiratory protection device of claim 1, wherein the mask comprises silicone, polypropylene, Thermoplastic Silicone Vulcanizate (TPSiV), polyolefin, polyphenylsulfone, high-density polyethylene (HDPE), acrylonitrile butadiene styrene (ABS), acrylic polymethyl methacrylate (acrylic PMMA), acetal copolymer (POM), polyetheretherketone (PEEK), polybutylene terephthalate (PBTR), or combinations thereof.

8. The sterilizable respiratory protection device of claim 1, wherein the at least one particulate air filter is adapted to filter at least 95% of airborne most penetrating particles.

9. The sterilizable respiratory protection device of claim 1, further comprising an identification tag.

10. A method for processing a respirator for reuse, comprising:
    providing a reusable respirator, comprising:
       at least one particulate air filter; and
       a unitary mask adapted for covering a portion of a user's face, said mask comprising:
          a face seal adapted to conform to a user's face around a nose and a mouth of the user;
          at least one outer shield portion forming a protrusion on an outer surface, said protrusion forming a protective pocket for housing the at least one particulate air filter; and
          at least one deformable opening formed through the at least one outer shield portion;
          wherein the at least one deformable opening is adapted to direct air flow through the outer surface for filtering by the at least one particulate air filter when open, and
          wherein the at least one deformable opening is adapted to prevent air flow through the outer surface for testing the seal when closed; and
    manually wiping the outer surface with a disinfectant.

11. The method for processing the respirator of claim 10, further comprising sterilizing the respirator as a single unit in an autoclave.

12. The method for processing the respirator of claim 10, further comprising applying at least one of: liquid disinfectants, gamma radiation, ethylene oxide, or vaporized hydrogen peroxide to the respirator.

13. The method for processing the respirator of claim 10, further comprising cleaning the respirator as a single unit in a dishwasher or a washing machine.

14. The method for processing the respirator of claim 10, further comprising sterilizing the respirator, wherein the at least one particulate air filter remains housed within the protective pocket during the sterilizing.

15. The method for processing the respirator of claim 10, wherein the respirator further comprises an identification tag, the method further comprising:
    scanning the identification tag to track at least one of: use of the respirator and processing of the respirator.

16. A system comprising:
    a sterilizable respiratory protection device, comprising:
       at least one particulate air filter; and
       a unitary mask adapted for covering a portion of a user's face, said mask comprising:
          a face seal adapted to conform to a user's face around a nose and a mouth of the user;
          at least one outer shield portion forming a protrusion on an outer surface, said protrusion forming a protective pocket for housing the at least one particulate air filter; and
          at least one deformable opening formed through the at least one outer shield portion;
          wherein the at least one deformable opening is adapted to direct air flow through the outer surface for filtering by the at least one particulate air filter when open, and
          wherein the at least one deformable opening is adapted to prevent air flow through the outer surface for testing the seal when closed; and
    a disinfection machine for cleaning the respiratory protection device.

17. The system of claim 16, wherein said respiratory protection device further comprises an identification tag; and said disinfection machine further comprises a tracking interface for allowing a user to track a disinfection process.

18. The system of claim 16, wherein said disinfection machine further comprises a controller having a processor configured to set a plurality of parameters for disinfection comprising at least one of: a temperature, a time duration, a concentration for a disinfectant solution, and a type of disinfection process.

19. The system of claim 16, wherein said disinfection machine further comprises an automatic detection mechanism for determining the age of the respiratory protection device.

20. The system of claim 16, wherein said disinfection machine further comprises racks or hooks configured to support the respiratory protection device.

* * * * *